United States Patent [19]

Conway

[11] Patent Number: 4,499,769

[45] Date of Patent: Feb. 19, 1985

[54] ACOUSTIC EMISSION MONITORING

[75] Inventor: Gregory J. Conway, Schenectady, N.Y.

[73] Assignee: The United States of America as represented by the Secretary of the Army, Washington, D.C.

[21] Appl. No.: 481,973

[22] Filed: Apr. 4, 1983

[51] Int. Cl.³ .......................... G01N 29/00; B21D 3/10
[52] U.S. Cl. ............................................ 73/587; 72/10; 72/19; 73/801
[58] Field of Search ..................... 73/587, 801; 72/10, 72/19, 20, 30

[56] References Cited

U.S. PATENT DOCUMENTS 3,713,312  1/1973  Galdabini ................................ 72/10
3,911,734  10/1975  Mehdizadeh ........................... 73/801
4,430,896  2/1984  Fujimori et al. ....................... 73/801
4,433,582  2/1984  Joosten ................................. 73/801

Primary Examiner—Anthony V. Ciarlante
Assistant Examiner—John E. Chapman, Jr.
Attorney, Agent, or Firm—Anthony T. Lane; Robert P. Gibson; Robert O. Richardson

[57] ABSTRACT

Acoustic emission monitoring is a non-destructive testing technique that detects ultra-high frequency sound that stressed metal emits. In straightening a gun tube the workpiece is at first under no stress, is elastically deformed (with total springback when pressure is released), is plastically deformed (with some springback upon release of pressure), or it cracks under too great a pressure. Each of these stages produces a distinctly different type of acoustic emission. By listening to the workpiece during the pressing operation the operator can be alerted as to the stage the workpiece is in and he can adjust his operation accordingly.

4 Claims, 3 Drawing Figures

U.S. Patent   Feb. 19, 1985   4,499,769
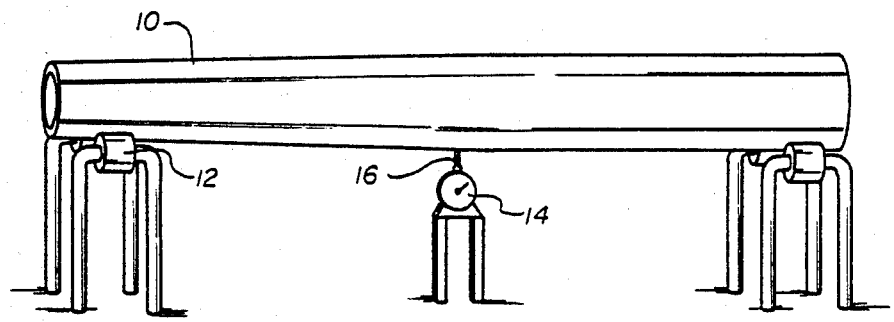
Fig_1_
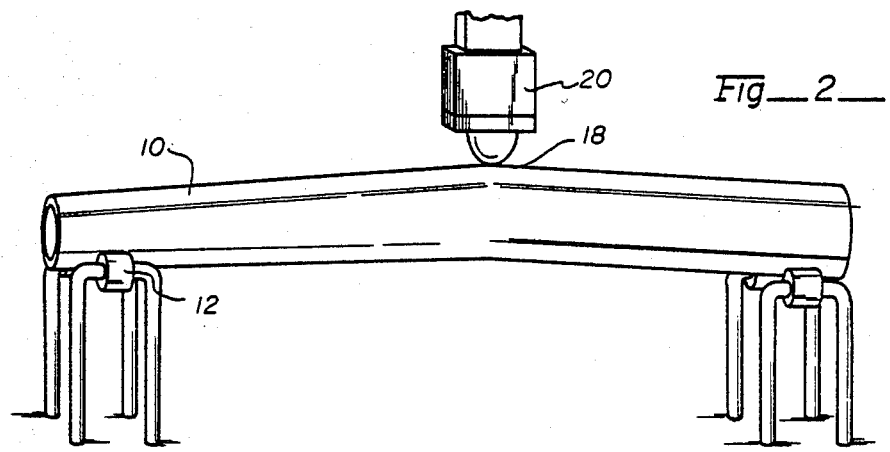
Fig_2_
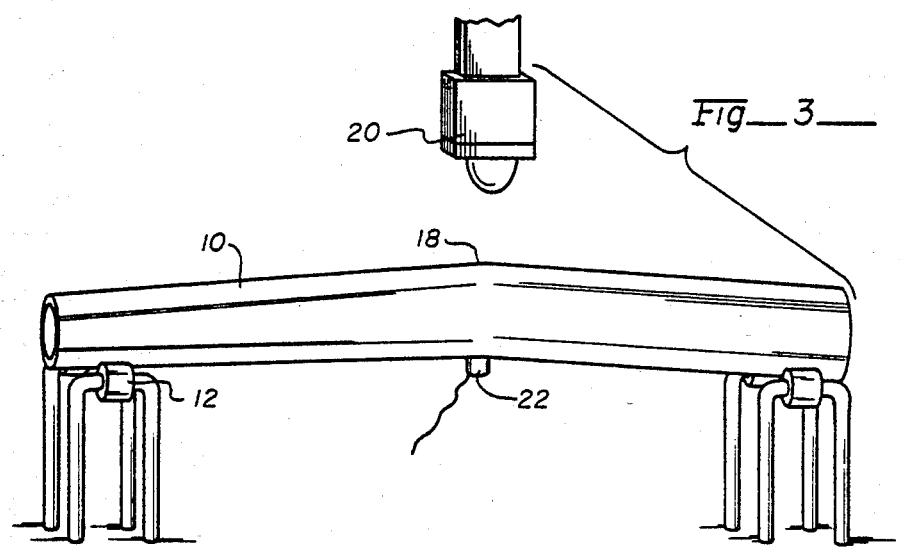
Fig_3_

ACOUSTIC EMISSION MONITORING

GOVERNMENT INTEREST

The invention described herein may be manufactured and/or used by or for the Government for governmental purposes without the payment of any royalty thereon.

BACKGROUND OF THE INVENTION

During the manufacture of gun and cannon tubes it is necessary to press the tubes in order to straighten them. Pressing is when the tube is set on blocks with the curve side up. A ram pushes down on the deformed area until it starts bending and permanently deforms into a straight tube. By analogy it is similar to straightening a bent nail with a hammer.

Unpredictable factors such as residual stresses, varying material properties, complexity of bend, history of the heat treat, forging and dimensional variations are different with each tube. Therefore the operation requires a high amount of operator judgment. By knowing which of the four stages the metal is being subjected to, the operator can adjust his operation accordingly.

It has been determined that each stage has its own distinctly different type of acoustic emission. Under a no stress condition no emission comes from the metal. Only background, hydraulic, mechanical, and electrical noises can be detected. Hydraulic and mechanical noises have relatively long ringdown counts whereas electrical noises have very short ringdown counts. Elastic deformation is characterized by the intermittent acoustic emission due to matrix relocation, fracture of occluded particles and voids. Plastic deformation is characterized by continuous emission of medium length ringdown count emission due to gross amounts of plane slippage, relocation and small amounts of micro-cracking.

Cracking is characterized by very high amplitude, high energy spikes that are substantially louder than elastic and plastic deformation and background noise.

BRIEF DESCRIPTION OF THE DRAWINGS

FIG. 1 is a schematic illustration of how the amount of wobble or runout in a warped or bent gun tube is determined.

FIG. 2 is a schematic illustration of how a bent gun tube is straightened.

FIG. 3 is a schematic illustration of tube straightening, using a transducer to obtain acoustic emission characteristics as the tube is being straightened.

DETAILED DESCRIPTION OF THE PREFERRED EMBODIMENT

Reference is now made to FIG. 1 wherein is shown a gun tube 10 mounted on pairs of rollers 12 at each end. Typically the gun tube is about 20 feet long. An indicator 14 has a tip 16 bearing against the gun tube 10 as it is rotated. With this indicator the amount of wobble and location of the high point of the bend of a warped gun tube can be determined.

In FIG. 2 there is shown the gun tube 10 with its high side 18 positioned upwardly. The bend here is exaggerated for clarity in illustration. In straightening the tube a hydraulic ram 20 bears against the high point 18 to force it downwardly to straighten the gun tube.

The operator's problem is to determine the amount of downward deflection to move the bent portion of the tube to straighten it. Gun barrel steel. ASME 4340, allows the gun barrel to spring back. The amount of deflection is measured and the next deflection is increased a little more, on the order of another $\frac{1}{8}$ inch deflection. This series of deflections is made until the gun barrel no longer returns fully to its original bent position. Eventually, as the deflections are increased, a point is reached when the gun barrel no longer springs all the way back but remains in its straightened position. Referring now to FIG. 3, there is show an acoustic emission sensor or transducer 22 attached to the underside of high point 18 of the gun tube 10. If the sensor and instrumentation is sensitive enough, the sensor may be placed on the end of the gun tube or even built into the ram 20. One such sensor is Model AC 375-LM made by the Acoustic Emission Technology (AET) Company with a magnet clamped to it. The magnet holds the sensor to the gun tube. The instrumentation, such as the AET 5000, is not shown. The transducer is connected to a pre-amplifier filter which amplifies the signal to eliminate environmental disturbances and to convert the signal into low impedance for transmission over long distances. Filters eliminate mechanical and electromagnetic noises. A threshold detector eliminates background noise and establishes a plateau above which the number of threshold crossings called counts can be made. The threshold crossings may then be plotted as a function of load, strain, time, or other external parameter. In the present case the operator learns to differentiate by sound.

Initially as the ram 20 engages the gun tube 10, crackling noises are heard like crunching sugar on a glass table with a spoon. When a hiss is heard in the operator's earphones, like FM static on the radio, the gun barrel is starting to bend permanently. The gun barrel will not spring back all the way. The downward movement of the hydraulic ram should be slowed down when this occurs. The hydraulic ram should be removed and the gun tube checked to see how much it was straightened. Ram pressure should then be reapplied until the hissing sound reappears to indicate more permanent bending. Again, the bending pressure is released to prevent destructive cracking. This process is repeated until the gun tube is straight.

With the use of acoustic emission checking, and a hissing sound in the operator's earphones, the press operator does not have to guess when the gun tube reaches the point during the bending that the tube will no longer spring back to its original bent position. The operator must always reach this point before releasing the ram pressure. Otherwise the tube will spring back to its bent position and it will never straighten out.

While the invention has been described in connection with specific embodiments thereof, it will be understood that it is capable of further modification and this application is intended to cover any variation, use, or adaption of the invention. It will, therefore, be recognized that the invention is not to be considered as limited to the precise embodiments shown and described, but is to be interpreted as broadly as permitted by the appended claims.

What is claimed is:

1. Acoustic emission monitoring of straightening gun tubes comprising the steps of:
   a. placing the high side of a bent gun tube upwardly as the gun tube is positioned in a horizontal position, b. placing an acoustic emission detection device on said tube, c. exerting a downward pressure on said high side until a plastic deformation state of said gun tube is reached as evidenced by said detection device sensing a hissing noise emission from said tube, and d. repeating the above steps until said gun tube is straight.

2. An acoustic emission monitoring method as set forth in claim 1 wherein said hissing noise is detected through said acoustic emission detection device.

3. An acoustic emission monitoring method as set forth in claim 1 wherein said gun tube is placed in a horizontal position and rotated to determine the high side of a bent gun tube in need of straightening.

4. An acoustic emission monitoring method as set forth in claim 1 wherein said acoustic emission detection device is placed on the underside of said high side of said gun tube.

* * * * *